United States Patent
Altmann et al.

(10) Patent No.: US 11,304,623 B2
(45) Date of Patent: Apr. 19, 2022

(54) INTEGRATION OF MEDICAL IMAGING AND LOCATION TRACKING

(71) Applicant: Biosense Webster (Israel) Ltd., Yokneam (IL)

(72) Inventors: Andres Claudio Altmann, Haifa (IL); Vadim Gliner, Haifa (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 704 days.

(21) Appl. No.: 16/231,990

(22) Filed: Dec. 25, 2018

(65) Prior Publication Data

US 2020/0196906 A1 Jun. 25, 2020

(51) Int. Cl.
*A61B 5/00* (2006.01)
*A61B 5/06* (2006.01)
*G06T 7/10* (2017.01)
*G06T 7/37* (2017.01)
*G06T 7/70* (2017.01)
*A61B 5/055* (2006.01)
*A61B 6/03* (2006.01)
(Continued)

(52) U.S. Cl.
CPC .............. *A61B 5/062* (2013.01); *A61B 5/055* (2013.01); *A61B 6/032* (2013.01); *A61B 6/466* (2013.01); *A61B 6/584* (2013.01); *G01R 33/58* (2013.01); *G06T 3/60* (2013.01); *G06T 7/10* (2017.01); *G06T 7/37* (2017.01); *G06T 7/70* (2017.01); *G06T 2207/10081* (2013.01); *G06T 2207/10088* (2013.01); *G06T 2207/30021* (2013.01); *G06T 2207/30204* (2013.01)

(58) Field of Classification Search
None
See application file for complete search history.

(56) References Cited

U.S. PATENT DOCUMENTS 9,474,466 B2 10/2016 Govari et al.
9,638,820 B2 5/2017 Govari et al.
(Continued)

OTHER PUBLICATIONS

Extended European Search Report for corresponding European patent application No. 19217848.1, dated Mar. 13, 2020.

*Primary Examiner* — Joel F Brutus

(74) *Attorney, Agent, or Firm* — Notaro, Michalos & Zaccaria P.C.

(57) ABSTRACT

A location tracking system maps anatomical structures in a first coordinate system, in a fixed position within a medical imaging system, which captures 3D images in a second coordinate system. The 3D images are converted to and stored in a standardized format in a third coordinate system in accordance with a first coordinate transformation. A first 3D image captured by the imaging system is registered with the first coordinate system so as to produce a second coordinate transformation. The first and second coordinate transformations are combined so as to derive a third coordinate transformation between the first and third coordinate systems. A second 3D image of a body of a subject, captured by the imaging system, is processed in order to extract image features in the third coordinate system. The extracted image features are joined with location data captured by the location tracking system by applying the third coordinate transformation.

20 Claims, 7 Drawing Sheets

(51) Int. Cl.
*A61B 6/00* (2006.01)
*G01R 33/58* (2006.01)
*G06T 3/60* (2006.01)

(56) References Cited

U.S. PATENT DOCUMENTS

| | | |
|---|---|---|
| 2006/0159323 A1 | 7/2006 | Sun et al. |
| 2007/0014453 A1 | 1/2007 | Nowinski et al. |
| 2009/0088628 A1 | 4/2009 | Klingenbeck-Regn |
| 2011/0054293 A1* | 3/2011 | Markowitz .......... G01S 5/0263 600/407 |
| 2012/0294498 A1 | 11/2012 | Popovic |
| 2015/0178448 A1 | 6/2015 | Zino et al. |
| 2015/0247944 A1 | 9/2015 | Govari et al. |
| 2017/0202633 A1 | 7/2017 | Liu |
| 2018/0185113 A1 | 7/2018 | Gregerson et al. |

* cited by examiner

INTEGRATION OF MEDICAL IMAGING AND LOCATION TRACKING

FIELD OF THE INVENTION

The present invention relates generally to medical devices, and particularly to combining images from multiple medical imaging and tracking devices.

BACKGROUND

In medical imaging, areas of subjects are imaged by medical imaging devices. In some cases, such as in cardiological diagnosis, the same areas are mapped with location tracking systems. The resulting images and maps may be presented in the coordinate system of the imaging or mapping device, as well as in standardized formats and coordinate systems, such as DICOM (Digital Imaging and Communications in Medicine). Various third-party programs are available for further analysis of the medical images.

Various methods of comparing images and maps from different devices are described in the patent literature. For example, U.S. Patent Application Publication 2015/0178448 describes a method for sending from a first medical device to a second medical device a request for data using a communication protocol that includes messages for conveying medical measurement results.

As a further example, U.S. Patent Application Publication 2007/0014453 describes a method for registering a measured MRI volume image with appropriate anatomical and blood supply territory Atlases to enable Atlas information to be mapped onto the measured MRI volume image.

As a yet further example, U.S. Patent Application Publication 2006/0159323 describes a system and method for automatically registering a three dimensional (3D) preoperative image of an anatomical structure with intra-operative electrophysiological (EP) points of a 3D electroanatomical (EA) image map of the anatomical structure.

As another example, U.S. Patent Application Publication 2009/0088628 describes a system and method that relates to enhanced medical workflows.

U.S. Pat. No. 9,474,466, whose disclosure is incorporated herein by reference, describes a location pad that includes a housing having a flat surface and multiple field generators. The multiple field generators are fixed to the housing and are configured to generate respective magnetic fields having respective axes that are perpendicular to the flat surface.

U.S. Pat. No. 9,638,820, whose disclosure is incorporated herein by reference, describes an apparatus that includes a detector assembly, a positioning unit, and interface circuitry. The detector assembly includes an array of multiple magnetic field detectors. The positioning unit is configured to fix the detector assembly at one or more known positions relative to a location pad, which generates magnetic fields for performing position measurements on an intra-body magnetic field detector using a positioning system. The interface circuitry is configured to output electrical signals that are produced by the magnetic field detectors of the detector assembly when the detector assembly is fixed at the known positions, so as to calibrate the position measurements performed by the positioning system.

SUMMARY

Embodiments of the present invention that are described hereinbelow provide improved methods for analyzing medical images.

There is therefore provided, in accordance with an embodiment of the invention, a method for registering images. The method includes installing a location tracking system, which is configured to map anatomical structures in a first coordinate system, in a fixed position within a medical imaging system, which captures three-dimensional (3D) images of the anatomical structures in a second coordinate system. The 3D images are converted to and stored in a standardized format in a third coordinate system in accordance with a first coordinate transformation between the second coordinate system and the third coordinate system. A first 3D image captured by the imaging system is registered with the first coordinate system so as to produce a second coordinate transformation between the first coordinate system and the second coordinate system. The first and second coordinate transformations are combined so as to derive a third coordinate transformation between the first coordinate system and the third coordinate system. A second 3D image of a body of a subject, captured by the imaging system, is processed in order to extract image features in the third coordinate system. The extracted image features are joined with location data captured by the location tracking system by applying the third coordinate transformation.

In a disclosed embodiment, the location tracking system comprises a magnetic tracking system, and registering the first 3D image with the first coordinate system includes inserting a jig including calibration targets into the medical imaging system, capturing the jig in the first 3D image, and measuring locations of the calibration targets.

In some embodiments, the medical imaging system includes a magnetic resonance imaging (MRI) system or a computerized tomography (CT) system.

In a disclosed embodiment, the third coordinate system is defined according to a Digital Imaging and Communications in Medicine (DICOM) protocol, and processing the second 3D image includes reading and processing the second 3D image by a software application complying with the DICOM protocol In some embodiments, processing the second 3D image includes at least one of rotating and segmenting the image.

Additionally or alternatively, the location data captured by the location tracking system includes a location of a distal end of a catheter within an anatomical structure in the body.

Further additionally or alternatively, joining the extracted image features with location data includes displaying the extracted image features and the location data concurrently on a display.

There is also provided, in accordance with an embodiment of the invention, an apparatus for displaying registered images. The apparatus includes a location tracking system, which is configured to map anatomical structures in a first coordinate system. A medical imaging system, within which the location tracking system is installed in a fixed position, is configured to capture three-dimensional (3D) images of the anatomical structures in a second coordinate system. The 3D images are converted to and stored in a standardized format in a third coordinate system in accordance with a first coordinate transformation between the second coordinate system and the third coordinate system.

A processor is configured to register a first 3D image captured by the imaging system with the first coordinate system so as to produce a second coordinate transformation between the first coordinate system and the second coordinate system. The processor combines the first and second coordinate transformations so as to derive a third coordinate transformation between the first coordinate system and the third coordinate system and processes a second 3D image of a body of a subject captured by the imaging system in order to extract image features in the third coordinate system. It joins the extracted image features with location data captured by the location tracking system after applying the third coordinate transformation to the location data.

The present invention will be more fully understood from the following detailed description of the embodiments thereof, taken together with the drawings in which:

DETAILED DESCRIPTION OF EMBODIMENTS

Overview

Figure 1:
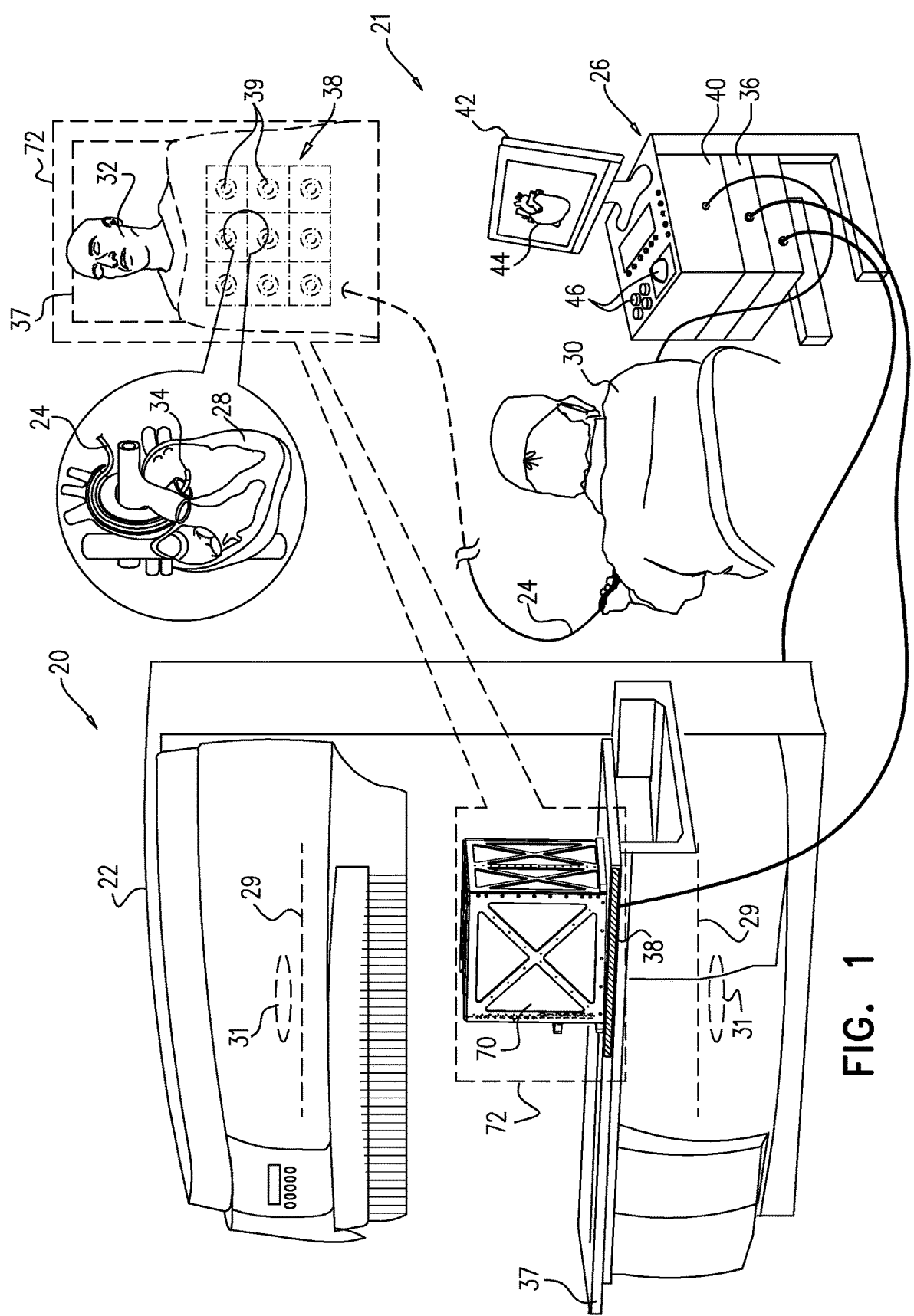
FIG. 1 is a schematic, pictorial illustration of a system comprising a location tracking system collocated with a medical imaging system, in accordance with an embodiment of the present invention.

Intra-body probes, such as catheters, are used in various therapeutic and diagnostic medical procedures. The catheter is inserted into the living body of a patient and navigated to the target region in a body cavity in order to perform the medical procedure. In magnetic field-based location tracking systems, an external magnetic field is applied to the patient's body. The magnetic field is produced by multiple magnetic field generators, e.g., field generating coils, typically fixed in a location pad in the vicinity of the patient. A sensor installed in the distal end of the catheter responds to the field by producing an electric signal. The signal is then used by the tracking system to locate the position and orientation of the catheter in the patient's body.

Magnetic location tracking of the catheter may be performed in or near a medical imaging system, as described, for example, in the references cited above in the Background section. Collocation of these two systems enables, inter alia, joint display of magnetic position tracking and medical imaging data.

DICOM (Digital Imaging and Communications in Medicine) is a standard protocol for, among other things, storing medical images according to the protocol. Numerous third-party applications that allow the stored medical image to be manipulated and/or analyzed are available, typically operating in the Visualization Toolkit (VTK) format. For example, such applications can be used to rotate and segment the image. Displaying the magnetic location tracking data, such as a location of a catheter, jointly with the rotated and segmented image would be very useful for the medical professional manipulating the catheter. In general, however, this sort of joint display can be performed only off-line, since the manipulated and/or analyzed image is stored in a DICOM coordinate system, whereas the location tracking system operates in a coordinate system typically defined by a location pad of that system.

The embodiments of the present invention that are described herein address the problem described above by providing simple and seamless registration between the location tracking system and the standard coordinate systems used in medical image processing applications, such as the DICOM coordinate system. The registration is performed initially between the location tracking system and the medical imaging system (such as an MRI scanner), and is then applied in deriving a coordinate transformation between the location tracking system and the image processing coordinate system. The initial registration can generally be performed only once, but the transformation that is derived can be used repeatedly thereafter in enabling location tracking results to be integrated with a variety of different applications that use the standard image processing coordinate system, in both real-time and off-line applications.

In the disclosed embodiments, a location tracking system, which maps anatomical structures in a locator coordinate system, is installed in a fixed position within a medical imaging system, which captures three-dimensional (3D) images of the anatomical structures in a device coordinate system. The 3D images are converted to and stored in a standardized format, such as DICOM, in a patient coordinate system in accordance with a first coordinate transformation between the device coordinate system and the patient coordinate system. A second coordinate transformation, between the locator coordinate system and the device coordinate system, is derived by registering a 3D image captured by the imaging system with the locator coordinate system. The first and second coordinate transformations are then combined to derive a third coordinate transformation between the locator coordinate system and the patient coordinate system.

Subsequently, when 3D images of a body of a subject are captured by the imaging system, and are then converted to and processed in the standardized patient coordinated system, for example in order to extract image features, the extracted image features can joined with location data created by the location tracking system in the subject's body by applying this same (third) coordinate transformation. The initial, one-time derivation of the transformation thus enables the use of any one of a variety of third-party applications to display a manipulated and/or processed medical image, while simultaneously viewing in real-time information provided by the location tracking system. This capability can be used, for example, to superimpose on the medical image an icon representing a catheter tracked by the location tracking system or electrophysiological mapping data gathered by the catheter.

System Description

FIG. 1 is a schematic, pictorial illustration of a system 20 comprising a location tracking system collocated with a medical imaging system, in accordance with an embodiment of the present invention. FIG. 1 and parts of the description that follows are based on the above-mentioned U.S. Pat. No. 9,638,820.

In the pictured embodiment, the location tracking system comprises a magnetic location tracking system 21, and the imaging system comprises a magnetic resonance imaging (MRI) scanner 22. The principles of the present invention, however, may similarly be applied to other sorts of medical imaging systems, such as coaxial tomography (CT) scanners, and other types of location tracking systems, such as impedance-based and ultrasonic tracking systems, as will be apparent to those skilled in the art. All such alternative embodiments are considered to be within the scope of the present invention.

Magnetic tracking system 21 can be realized as, for example, the Carto® 3 system, produced by Biosense Webster, of 33 Technology Drive, Irvine, Calif. 92618 USA. MRI scanner 22 can be realized as, for example, the MAGNETOM Aera, produced by Siemens Healthcare GmbH, of Henkestrasse 127, 91052 Erlangen, Germany.

Magnetic tracking system 21 comprises an intra-body probe 24, such as a catheter, and a control console 26. An operator 30, such as a cardiologist, percutaneously navigates catheter 24 through the vascular system of a patient 32 so that a distal end 34 of the catheter 24 enters a body cavity, herein assumed to be the cardiac chamber. Catheter 24 may be used, for example, for mapping electrical potentials in a chamber of a heart 28 of patient 32 with multiple electrodes disposed near distal end 34 of catheter 24 that contact the tissue of the heart cavity at multiple points. In alternative embodiments, catheter 24 may be used, mutatis mutandis, for other therapeutic and/or diagnostic functions in the heart or other body organs.

Console 26 uses magnetic position sensing to determine the orientation and position coordinates of distal end 34 of catheter 24 inside heart 28. Console 26 operates a driver circuit 36, which drives one or more magnetic field generators 39 in a location pad 38 below the patient's torso on a table 37 as shown in a dotted inset 72 in the upper right hand corner of FIG. 1. Alternatively, location pad 38 may be have a different shape and be positioned in a different location, for example above patient 32, in order to comply with the space requirements of a specific MRI scanner 22.

A position sensor installed in distal end 34 generates electrical signals in response to the magnetic fields generated by location pad 38, thereby enabling console 26 to determine the position and orientation of the distal end with respect to the location pad, and thus, the position and orientation within heart 28 of patient 32.

MRI scanner 22 comprises magnetic field coils 29, including field gradient coils, which together generate a spatially variant magnetic field. The spatially variant magnetic field provides spatial localization for radio frequency (RF) signals generated by the scanner. In addition, the scanner comprises transmit/receive coils 31. In a transmit mode, coils 31 radiate RF energy to patient 32, the RF energy interacting with the nuclear spins of the patient's tissue and thereby realigning the magnetic moments of the nuclei away from their equilibrium positions. In a receive mode, coils 31 detect RF signals received from the patient's tissue as the tissue nuclei relax to their equilibrium state.

MRI scanner 22 depicted in FIG. 1 comprises a structure that is open along one side of patient 32. Alternatively, MRI scanner 22 may have a different, tube-like structure, such as for example the Siemens MAGNETOM Aera scanner previously referred to.

Table 37 in MRI scanner 22 normally supports patient 32, as shown in inset 72. In the pictured embodiment, however, a registration jig 70 is placed on table 37 in order to register the coordinate system of MRI scanner 22 with the coordinate system of the magnetic catheter tracking system, as is described in the above-mentioned U.S. Pat. No. 9,638,820. The details of the registration process will be described further below. Jig 70 is placed on table 37 above location pad 38 within MRI scanner 22 in the same region where the torso of patient 32 would normally be positioned on table 37.

A processor 40 has multiple functions in the embodiment shown in FIG. 1. First, processor 40 is configured to receive electrical signals induced in the position sensor at catheter distal end 34 in response to the magnetic field generated by location pad 38 via interface circuitry (not shown). Processor 40 uses the received electrical signals to locate the catheter in the patient's body.

Secondly, processor 40 operates MRI scanner 22 by using circuitry to control MRI coils 29, including forming required magnetic field gradients, as well as other circuitry to operate transmit/receive coils 31 around patient 32. Processor 40 acquires MRI data within a volume of interest 308 (shown in FIG. 4), as will be described below. Volume of interest 308, for example, may comprise heart 28 of patient 32. Using the MRI data, processor 40 displays an image 44 of heart 28 to operator 30 on a display 42. The position of catheter 24 acquired by magnetic tracking system 21 can be superimposed on image 44 of heart 28 on display 42 acquired by MRI scanner 22. As will be further described below, operator 30 may process the MRI data using a third-party application, and display a processed medical image 446 (FIG. 6) with an image of catheter 24 superimposed thereon.

Processor 40 typically comprises a general-purpose computer, which is programmed in software to carry out the functions that are described herein. The software may be downloaded to processor 40 in electronic form, over a network, for example, or it may be provided on non-transitory tangible media, such as optical, magnetic or electronic memory media. Alternatively, some or all of the functions of processor 40 may be carried out by dedicated or programmable digital hardware components, or by using a combination of hardware and software elements.

Alternatively, the functions of processor 40 may be split between two or more processors, for example, one processor managing the magnetic position tracking system and one managing the MRI scanner. More generally, the embodiment shown in FIG. 1 is presented merely for conceptual clarity, and not by way of limitation of the embodiments of the present invention. MRI scanner 22 and magnetic tracking system 21 may have separate processors for each system and not shared as in the embodiment shown in system 20. Single or separate displays may be used for MRI scanner 22 and magnetic tracking system 21.

Figure 2:
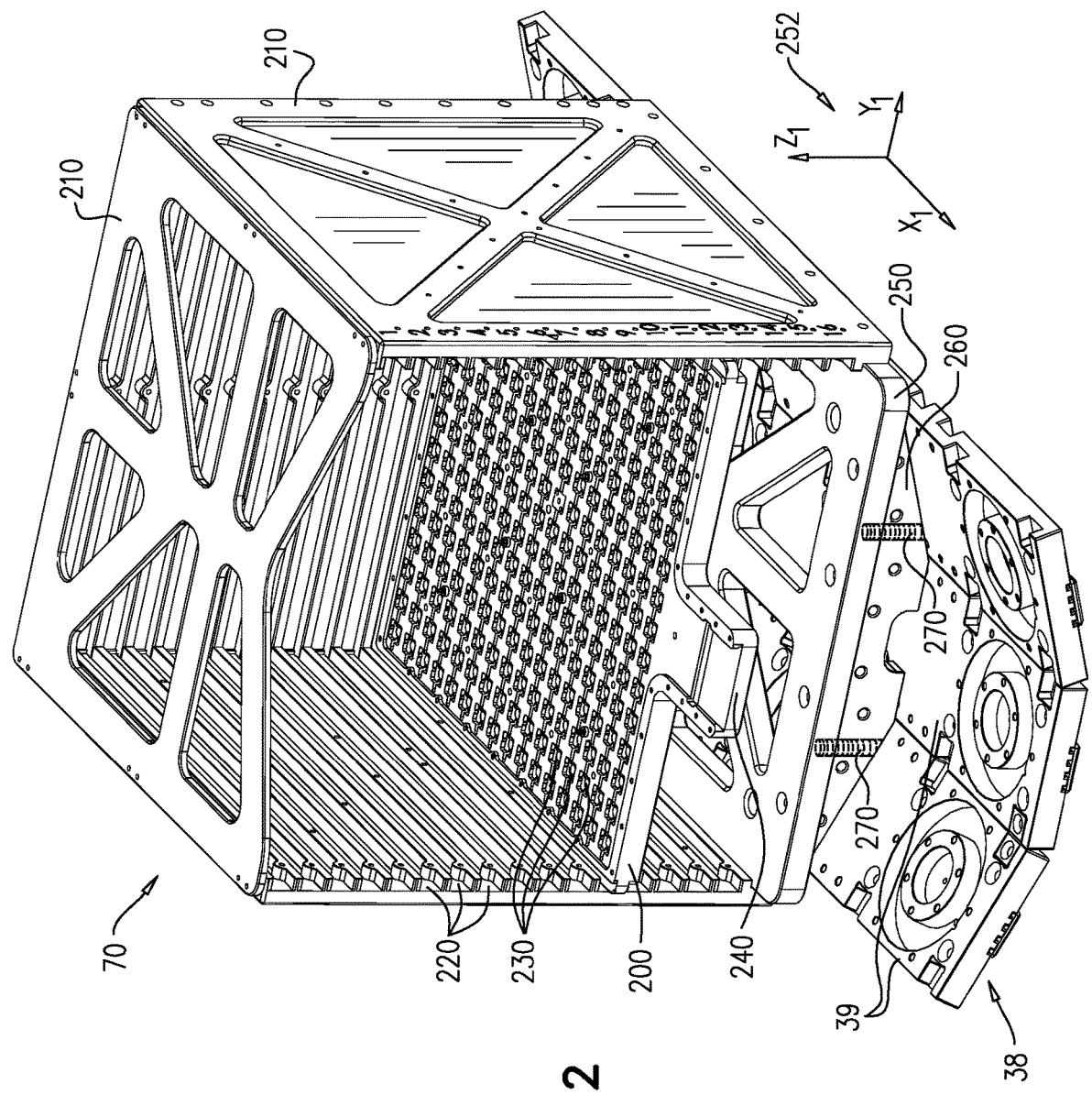
FIG. 2 is a schematic, pictorial illustration of a registration jig, in accordance with an embodiment of the present invention.

Registration of the Coordinate Systems of the MRI Scanner and the Magnetic Tracking System FIG. 2 is a schematic, pictorial illustration of registration jig 70, in accordance with an embodiment of the present invention. Registration jig 70 comprises a positioning unit 210 having multiple slots 220 that are separated by a fixed, predefined distance between adjacent slots. Jig 70 is placed above location pad 38, as shown in FIG. 1. For other configurations and locations of location pad 38, jig 70 may be placed in a different position. For example, for a location pad 38 positioned against the interior ceiling of MRI scanner 22, jig 70 may be placed below it.

A registration assembly 200, also referred to as a shelf, comprises an array of cubical receptacles 230. Other forms of receptacles 230 are also applicable, as will be shown in FIG. 3. Registration assembly 200 can be inserted into any of slots 220 in positioning unit 210. The multiple slots in positioning unit 210 are configured to fix registration assembly 200 at one or more known positions relative to location pad 38. In the embodiment shown in FIG. 2, the slots 220 control the position (e.g., the height) of registration assembly 200 with respect to location pad 38.

A baseplate 250 of positioning unit 210 is connected to a conformal adapter 260, which is configured to fit and conform to the shape of location pad 38 such that the array of receptacles 230 will be in the $X_1$-$Y_1$ plane at a fixed distance above the location pad and orthogonal to the $Z_1$-axis. The $X_1$-, $Y_1$-, and $Z_1$-axes are the coordinate axes of a Cartesian first coordinate system 252. Adapter 260 may be machined, or formed, by any suitable process so as to conform to the curvature of location pad 38. Location pad 38 is shown here as an example, and is described in more detail in the above-mentioned U.S. Pat. No. 9,638,820. Alternatively, other sorts of location pads and calibration jigs may be used for the present purposes, as will be apparent to those skilled in the art after reading the present description.

Figure 3:
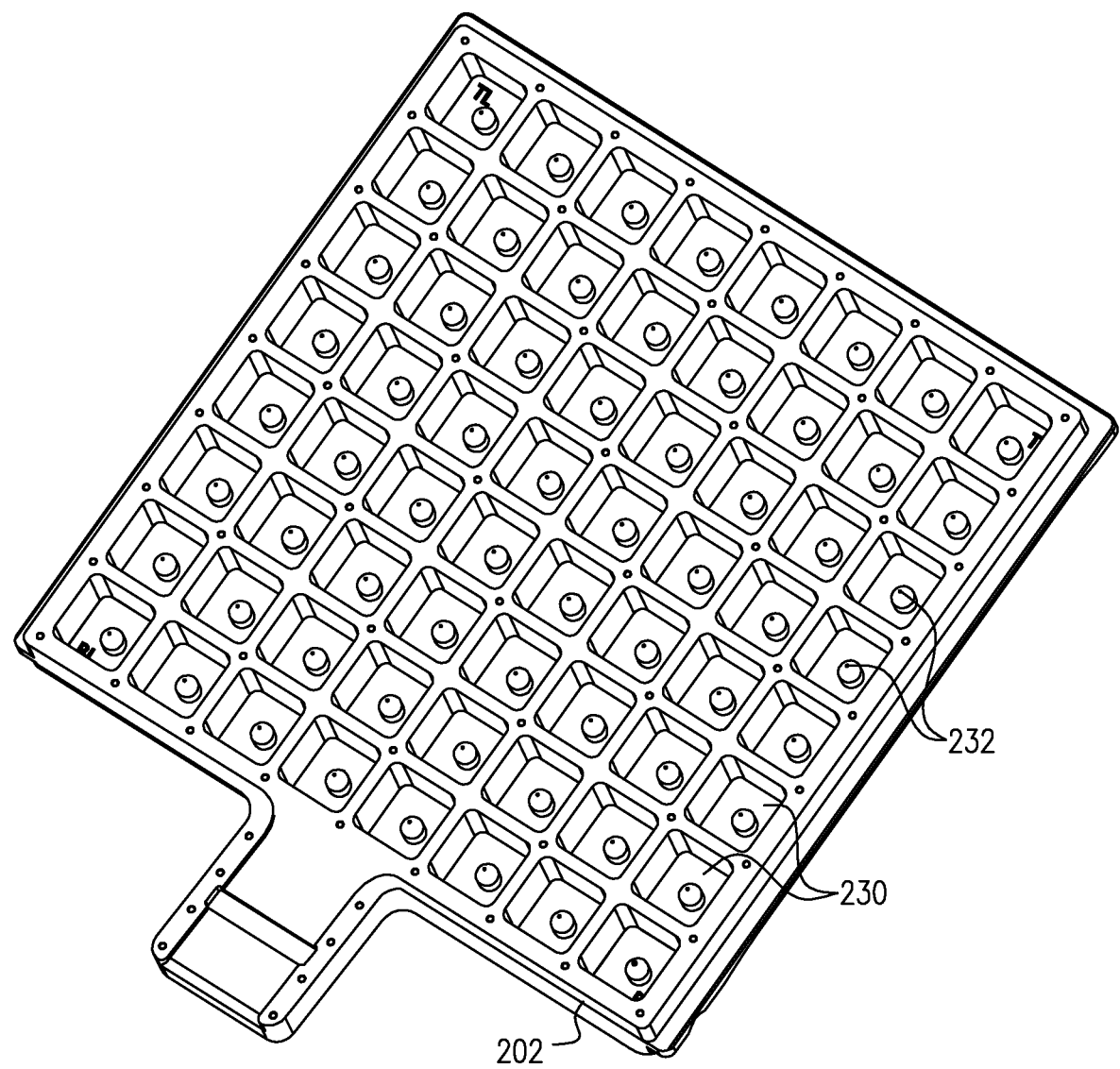
FIG. 3 is a schematic, pictorial illustration of a registration assembly, in accordance with an embodiment of the present invention.

FIG. 3 is a schematic, pictorial illustration of a registration assembly 202, in accordance with an embodiment of the present invention. Registration assembly 202 serves the same purpose as registration assembly 200 of FIG. 2 and can similarly be used in jig 70.

Registration assembly 202 comprises an 8×8 array of receptacles 230, with a cone-shaped protrusion 232 in the center of each receptacle. Receptacles 230 are filled with an MRI-detectible fluid, such as water, and serve as MRI image reference markers. Either all or a subset of receptacles 230 are filled with the fluid. Filling an asymmetrical subset of receptacles 230 will facilitate a unique determination of the orientation of the subsequent MRI image. The fluid may be sealed in the volume of the receptacles by any suitable procedure. Alternatively, receptacles 230 may be left unsealed. Further alternatively, the reference markers may comprise MRI-detectible fluid-filled spheres with known radii, as described in the above-mentioned U.S. Pat. No. 9,638,820.

In alternative embodiments, comprising different types of medical imaging systems, registration assembly 202 may comprise reference markers of a different substance. For example, for an embodiment wherein medical imaging system comprises an x-ray based imager, such as a computerized tomography (CT) system, the reference markers may be filled with a substance opaque or partially opaque to x-rays, such as calcium.

When registration assembly 202 is placed in positioning unit 210, MRI scanner 22 images the fluid-filled registration array of receptacles 230, and processor 40 registers the known positions of these receptacles in system 20 relative to location pad 38. The known positions of fluid-filled receptacles 230, acting as MRI reference markers, are then used to register the coordinate systems of MRI scanner 22 and magnetic tracking system 21. Stated differently, processor 40 uses the array of multiple MRI reference markers 230 fixed by positioning unit 210 in at least one known position relative to location pad 38 for registering the coordinate systems.

To improve the resolution, the positioning unit can be configured to continuously vary the known position of the assembly within the separation distance between adjacent slots 220 so as to continuously fine tune the height in the $Z_1$-direction as shown in FIG. 2, after the assembly is fixed in a particular slot. For example, one or more turn screws 270 can be embedded in conformal adaptor 260 and oriented in the $Z_1$-direction such that rotating the turn screws 270 moves, or jacks up, baseplate 250, and thus, adjusts the $Z_1$-position of unit 210 relative to conformal adapter 260.

The embodiments shown in FIGS. 2-3 are depicted merely for conceptual clarity, as examples of devices and methods that can be used in registering tracking system 21 and MRI scanner 22, and not by way of limitation of the embodiments of the present invention. Other sorts of registration devices and methods will be apparent to those skilled in the art after reading the present description and are considered to be within the scope of the present invention.

Coordinate Systems

Figure 4:
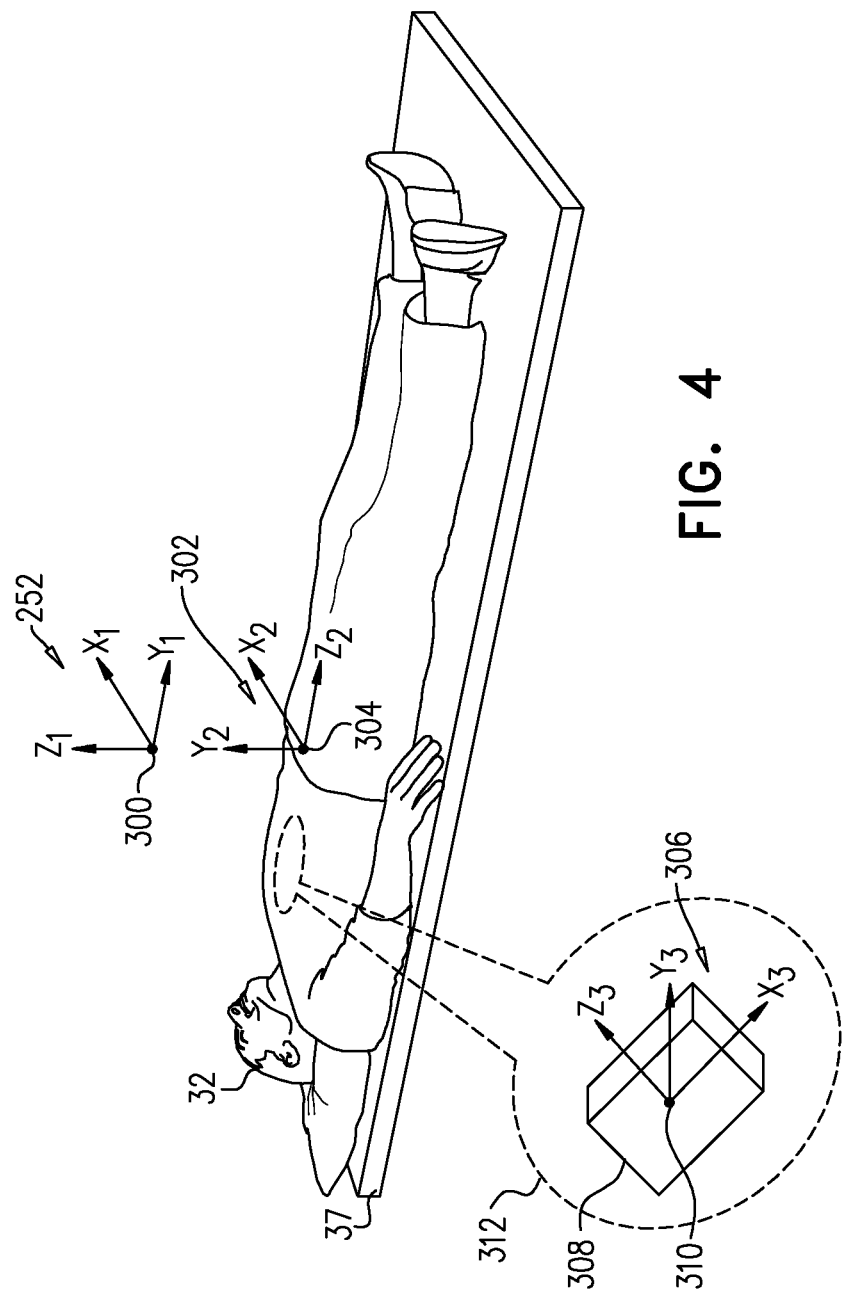
FIG. 4 is a schematic pictorial view of three coordinate systems, in accordance with an embodiment of the present invention.

FIG. 4 is a schematic pictorial view of three coordinate systems, which undergo registration and transformation in accordance with an embodiment of the present invention. Three right-handed Cartesian coordinate systems are shown in the figure, as they relate to table 37 of MRI scanner 22 and to patient 32:

1. First coordinate system 252 (shown in FIG. 2), labelled by axes $X_1$, $Y_1$, and $Z_1$, is the coordinate system of magnetic tracking system 21. This coordinate system is also called the Locator Coordinate System (LCS). Coordinate system 252 is oriented with its $Z_1$-axis perpendicular to table 37 and $Y_1$-axis along the long axis of the table. Depending on the location and orientation of location pad 38, the $Z_1$-axis points either up or down. An origin 300 of first coordinate system 252 is located at a user-defined point referenced to location pad 38.

2. A second coordinate system 302 is the coordinate system of MRI scanner 22, also called the Device Coordinate System (DCS). It is oriented with its $Z_2$-axis along the long axis of table 37, and $Y_2$-axis perpendicular to the table. Its origin 304 is located in the isocenter of MRI scanner 22, wherein the isocenter is the center of symmetry of the magnetic field of the scanner, and is known to the scanner. Thus second coordinate system 302 is permanently fixed to MRI scanner 22.

3. A third coordinate system 306 is the Patient Coordinate System (PCS). Third coordinate system 306 is aligned with the sides of volume of interest 308 (commonly a rectangular parallelepiped), with its origin 310 centered within the volume of interest. Volume of interest 308, shown in a dotted inset 312, is defined by operator 30, using control console 26, with reference to a low-resolution MRI scan, wherein the volume of interest encompasses the anatomical volume to be imaged at high resolution, such as, for example, heart 28. Thus, third coordinate system 306 is stored within processor 40 along with second coordinate system 302. Volume of interest 308, and with it, third coordinate system 306, is in general both shifted and rotated with respect to second coordinate system 302, by known amounts recorded by processor 40. Third coordinate system 306 is the system used by the DICOM protocol, and consequently by third-party applications for manipulating medical images stored as DICOM files.

The three coordinate systems are summarized in Table 1, below.

TABLE 1

Summary of coordinate systems

| Coordinate system | Label | Reference structure | Alternative name | DICOM coordinates |
|---|---|---|---|---|
| First coordinate system | 252 | Magnetic tracking system 21 | Location Coordinate System (LCS) | No |
| Second coordinate system | 302 | MRI scanner 22 | Device Coordinate system (DCS) | No |
| Third coordinate system | 306 | Volume of interest 308 | Patient Coordinate System (PCS) | Yes |

Coordinate Transformations

Figure 5:
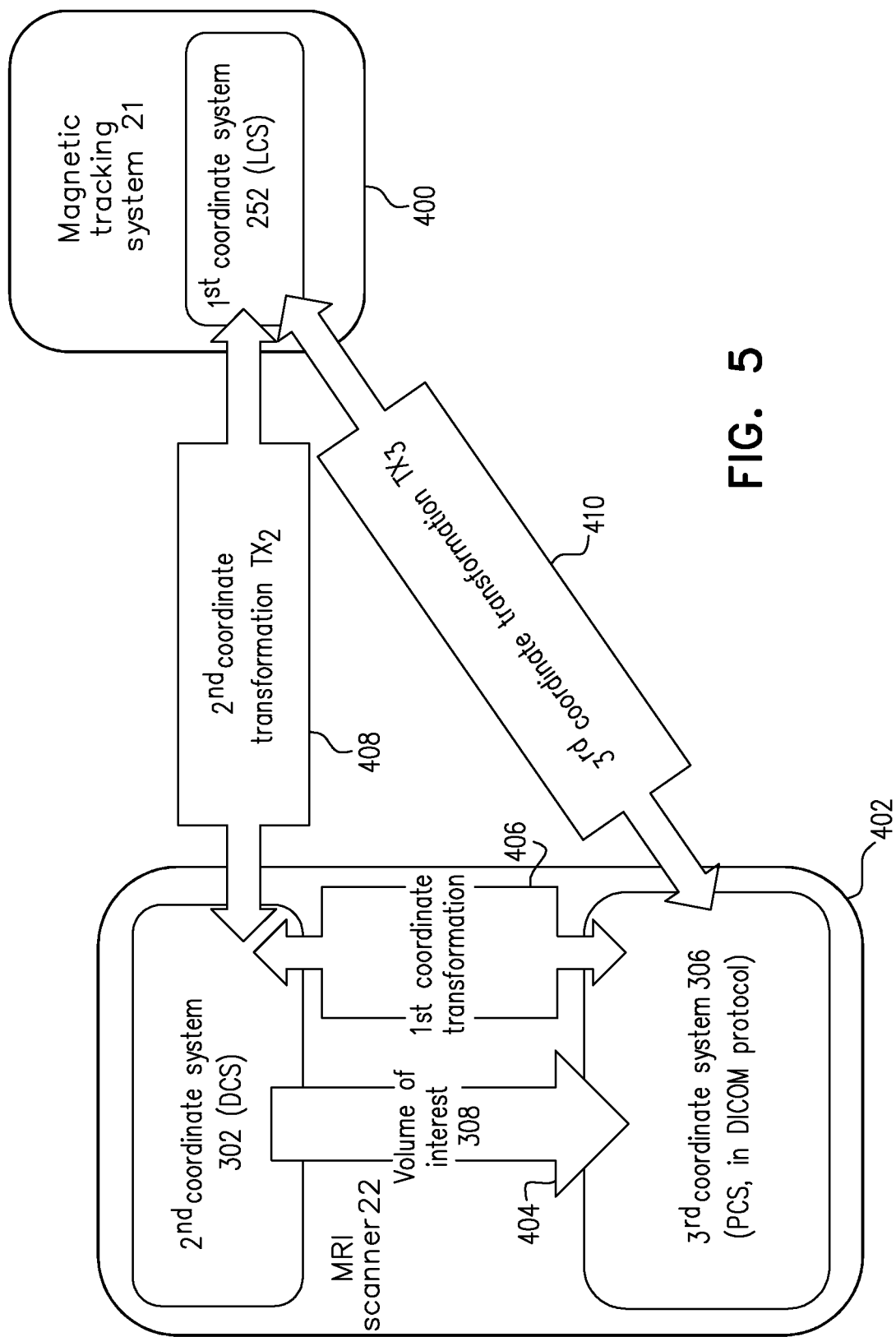
FIG. 5 is a block diagram that schematically illustrates three coordinate transformations, in accordance with an embodiment of the present invention.

FIG. 5 is a block diagram that schematically illustrates coordinate transformations between the coordinate systems described above, in accordance with an embodiment of the present invention.

A block 400 refers to magnetic tracking system 21 with its first coordinate system 252. A block 402 refers to MRI scanner 22 with its two coordinate systems: second coordinate system 302 and third coordinate system 306. An arrow 404 represents the definition of third coordinate system 306, according to the DICOM-protocol, by volume of interest 308. The spatial relationship between second and third coordinate systems 302 and 306, respectively, is known to processor 40, and thus the processor calculates a first coordinate transformation $TX_1$, shown as a double arrow 406, which is the transformation between the second and third coordinate systems.

A second coordinate transformation $TX_2$, shown as a double arrow 408, is the transformation between first and second coordinate systems 252 and 302. It is calculated by processor 40 based on the registration procedure described above.

A third coordinate transformation $TX_3$, shown as a double arrow 410, is calculated by processor 40 as a product between first and second coordinate transformations $TX_1$ and $TX_2$. Third coordinate transformation $TX_3$ conveys the transformation between first coordinate system 252 and third coordinate system 306, i.e. between the coordinates of magnetic tracking system 21 in LCS and the coordinates in PCS according to the DICOM-protocol.

The algorithm applied by processor 40 for the coordinate transformations is based on 4×4 matrices, wherein each matrix implements one specific action. The individual 4×4 matrices and their effects are listed in Table 2, below.

TABLE 2

Individual coordinate transformation matrices

| Matrix | Effect |
|---|---|
| $\begin{bmatrix} 1 & 0 & 0 & 0 \\ 0 & \cos\varphi & -\sin\varphi & 0 \\ 0 & \sin\varphi & \cos\varphi & 0 \\ 0 & 0 & 0 & 1 \end{bmatrix}$ | Rotation about x-axis by angle $\varphi$ |
| $\begin{bmatrix} \cos\varphi & 0 & \sin\varphi & 0 \\ 0 & 1 & 0 & 0 \\ -\sin\varphi & 0 & \cos\varphi & 0 \\ 0 & 0 & 0 & 1 \end{bmatrix}$ | Rotation about y-axis by angle $\varphi$ |
| $\begin{bmatrix} \cos\varphi & -\sin\varphi & 0 & 0 \\ \sin\varphi & \cos\varphi & 0 & 0 \\ 0 & 0 & 1 & 0 \\ 0 & 0 & 0 & 1 \end{bmatrix}$ | Rotation about z-axis by angle $\varphi$ |
| $\begin{bmatrix} 1 & 0 & 0 & Tx \\ 0 & 1 & 0 & Ty \\ 0 & 0 & 1 & Tz \\ 0 & 0 & 0 & 1 \end{bmatrix}$ | 3D translation by Tx, Ty, and Tz |
| $\begin{bmatrix} Sx & 0 & 0 & 0 \\ 0 & Sy & 0 & 0 \\ 0 & 0 & Sz & 0 \\ 0 & 0 & 0 & 1 \end{bmatrix}$ | 3D scaling by Sx, Sy, and Sz |

The individual coordinate transformation matrices of Table 2 or their products effect a coordinate transformation by multiplying a 4×1 vector $$\begin{bmatrix} x \\ y \\ z \\ 1 \end{bmatrix},$$

wherein the first three elements are the xyz-coordinates, and the fourth element is required for the translation operation. Thus coordinate transformations $TX_1$ and $TX_2$ are 4×4 matrices, and coordinate transformation $TX_3$ is a matrix product of the former two matrices.

Figure 6:
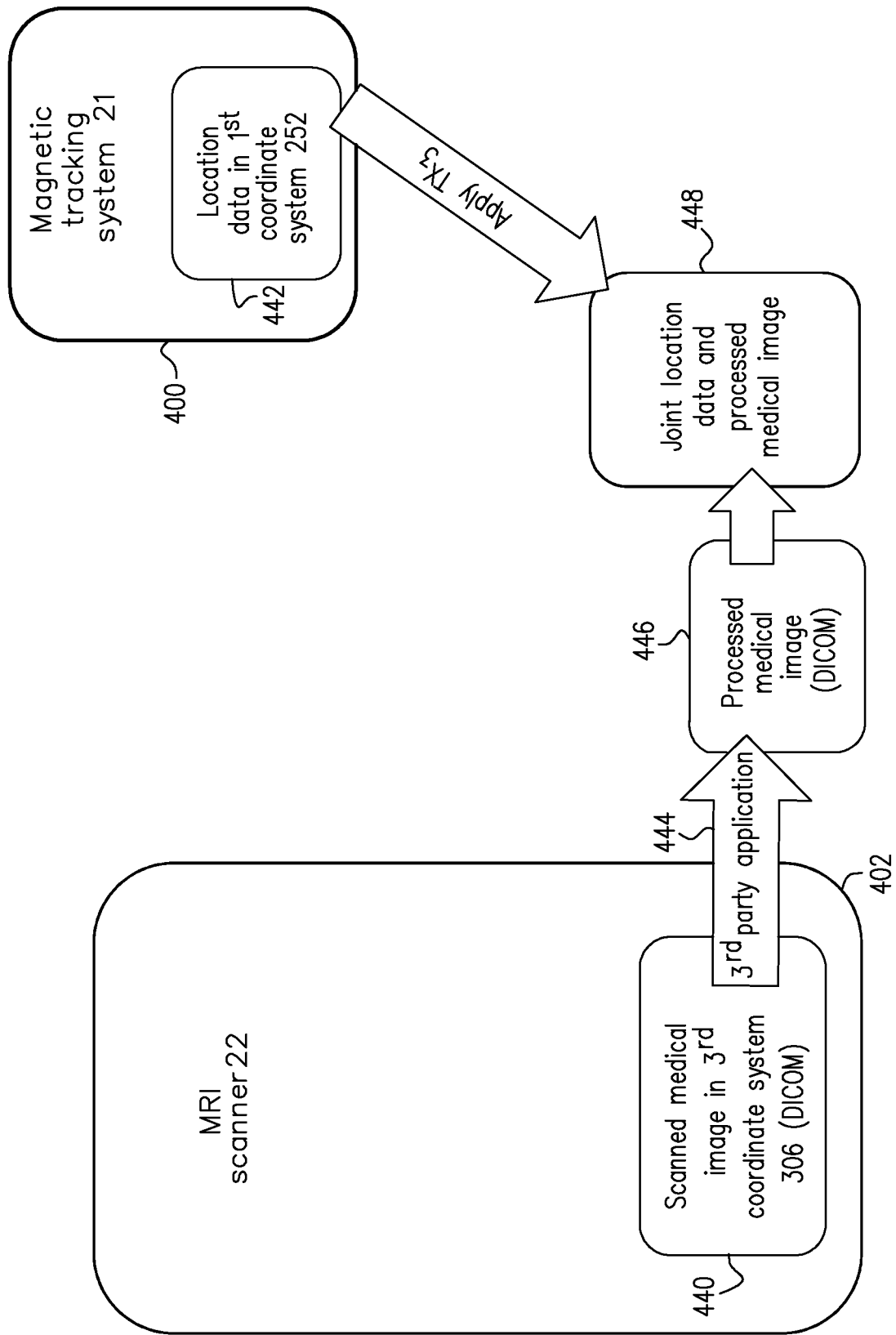
FIG. 6 is a block diagram that schematically illustrates a process for joining of a medical image, processed by a third-party application, and location data, in accordance with an embodiment of the present invention.

FIG. 6 is a block diagram that schematically illustrates a process for joining of a medical image 440, processed by a third-party application in DICOM coordinates, for example, and location data 442, in accordance with an embodiment of the present invention.

MRI scanner 22 produces a medical image 440 of patient in third coordinate system 306, i.e., in the DICOM coordinate system. Medical image 440 is processed by processor 40 using a third-party application, indicated by an arrow 444, giving a processed medical image 446, which is also represented in the DICOM coordinates. The processing of medical image 440 comprises, for example, rotating and/or segmenting the image. Magnetic tracking system 21 produces location data 442 of catheter 24 in first coordinate system 252. Third coordinate transformation $TX_3$ is applied by processor 40 to location data 442, thus transforming the location data from first coordinate system 252 into third coordinate system 306, i.e., into the DICOM coordinate system.

Processor 40 then presents on display 42 a joint image 448 of catheter 24 superimposed on processed medical image 446. No recalibration or re-registration is needed in order to register coordinate systems 252 and 306, since the transformation that was previously computed can be used for this purpose. The same method can be used to display other sorts of data provided by magnetic tracking system 21, such as marking or coloring processed medical image 446 to show electrophysiological data collected by the catheter.

Figure 7:
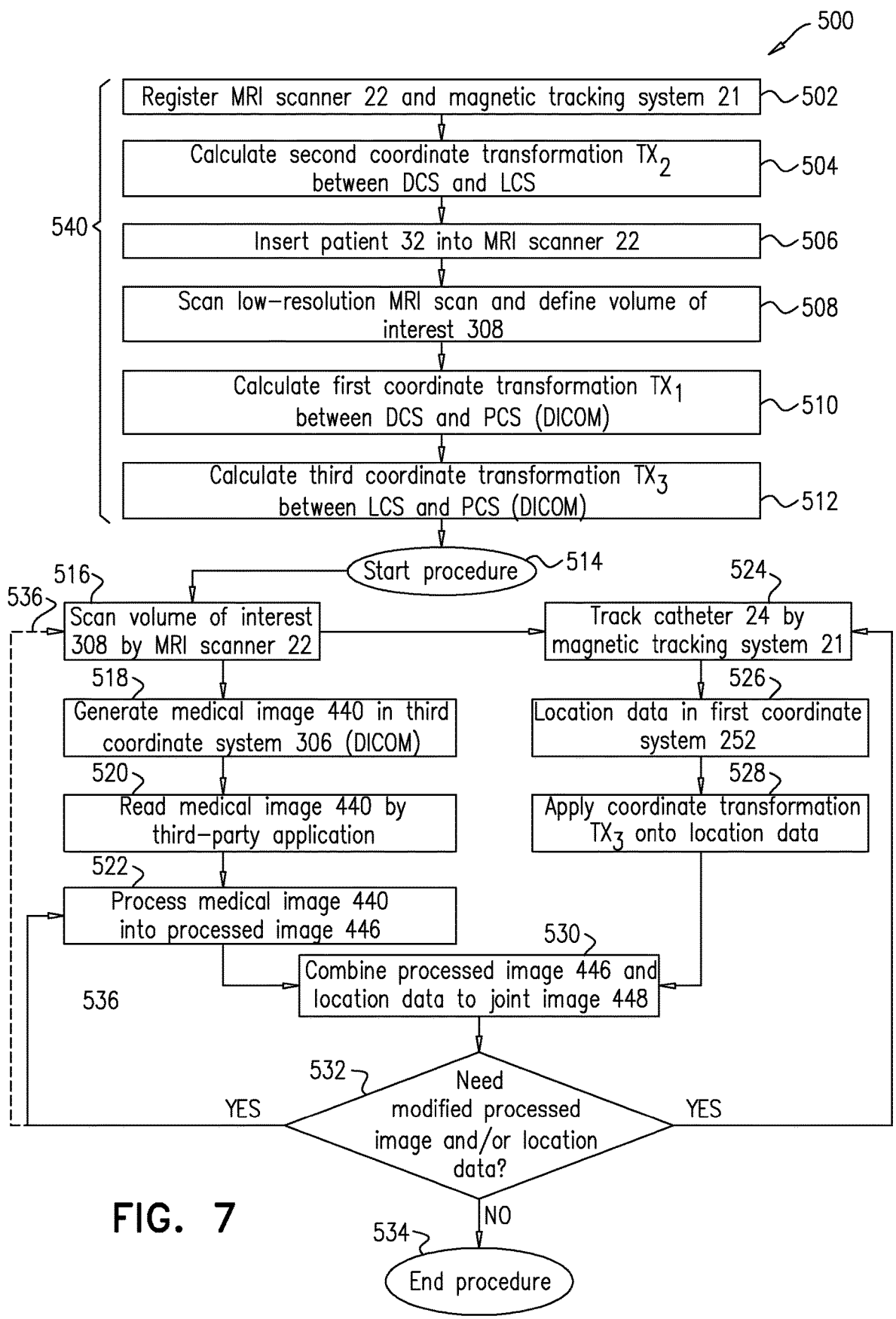
FIG. 7 is a flowchart that schematically illustrates the process for combining and displaying a medical image and location data, in accordance with an embodiment of the invention.

FIG. 7 is a flowchart 500 that schematically illustrates a process for combining and displaying medical image and location data, in accordance with an embodiment of the invention.

A preparatory stage 540 starts with a registration step 502, wherein MRI scanner 22 and magnetic tracking system 21 are registered with each other, as described above. In a second coordinate transformation step 504, processor 40 calculates a second coordinate transformation $TX_2$ between second coordinate system 302 (device coordinate system, DCS) and first coordinate system 252 (location coordinate system, LCS).

In a patient insertion step 506, patient 32 is inserted into MRI scanner 22. In a volume of interest step 508, a low-resolution scan of patient 32 is performed with MRI scanner 22, and operator 30 defines, using control console 26, volume of interest 308 as the volume for subsequent high-resolution MRI scans. In a first coordinate transformation step 510, first coordinate transformation $TX_1$ is calculated between second coordinate system 302 (DCS) and third coordinate system 306 (patient coordinate system, PCS, in DICOM coordinates).

In a third coordinate transformation step 512, third coordinate transformation $TX_3$ is calculated between first coordinate system 252 (LCS) and third coordinate system 306 (PCS) as a product of $TX_1$ and $TX_2$. Step 512 completes preparatory stage 540.

In a start step 514, imaging of patient 32 and location tracking are started, although not necessarily concurrently, as is detailed below. In an MRI scan step 516, volume of interest 308 is scanned by MRI scanner with a high-resolution scan, generating medical image 440 in third coordinate system 306 in an image generation step 518. In a read step 520, medical image 440 is read by a processor running a third-party software application, and further processed by the application in a processing step 522 to produce processed image 446.

Location tracking of, for example, catheter 24 by magnetic tracking system 21 is started in a tracking step 524. Location tracking can be delayed until after MRI scan step 516 is completed, in order to avoid interference with the location tracking by the magnetic fields of MRI scanner 22. In a location data step 526, the location tracking produces location data in first coordinate system 252. In a transformation application step 528, coordinate transformation $TX_3$ is applied to location data from location data step 526, thereby transforming the location data into DICOM-coordinates.

In a combination step 530, processed image 446 from processing step 522 and the location data in DICOM-coordinates from transformation application step 528 are combined to create joint image 448, which may be shown on display 42 and viewed by operator 30. In all of steps 518, 520, 522, 528, and 530, both the medical image data and location data are expressed in DICOM-coordinates in order to enable the use of a third-party application and joint display of the image data and the location data.

In a decision step 532, operator 30 decides whether he/she desires to modify processed image 446 by the third-party application by, for example, rotating the image or segmenting it. In decision step 532, operator 30 may also decide to move catheter 24 and thus acquire new location data. Both modifying processed image 446 and moving catheter 24 activate again steps 522 and 524, respectively. The loops from decision step 532 through steps 522 and 524 may happen in a continuous fashion. For example, operator may move catheter 24 continuously and observe the changing location of the catheter on joint image 448. Operator 30 may also, for example, rotate processed image 446 continuously while observing the location of catheter in the rotating image. Operator 30 may further continuously change both processed image 446 and location of catheter 24 and observe these changes in a dynamically changing joint image 448.

The medical procedure that operator 30 is performing may change the shape and dimensions of the anatomical details observed within volume of interest 308, for example by surgically operating on the organ in the volume of interest. Based on the operator's experience and observations, he/she may decide that an updated medical image is required. In such a case, operator 30 may initiate a new MRI scan as shown by a dotted arrow 536. Location tracking can be stopped while MRI scanner 22 is acquiring a new scan in MRI scan step 516. Once the scan is completed, the process returns to the two paths starting with steps 518 and 524.

The procedure ends in an end step 534.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for registering images, the method comprising:
    installing a location tracking system, which is configured to map anatomical structures in a first coordinate system, in a fixed position within a medical imaging system, which captures three-dimensional (3D) images of the anatomical structures in a second coordinate system, wherein the three-dimensional (3D) images are converted to and stored in a standardized format in a third coordinate system in accordance with a first coordinate transformation between the second coordinate system and the third coordinate system;
    registering a first 3D image captured by the imaging system with the first coordinate system so as to produce a second coordinate transformation between the first coordinate system and the second coordinate system;
    combining the first coordinate transformation and the second coordinate transformation so as to derive a third coordinate transformation between the first coordinate system and the third coordinate system;
    processing a second 3D image of a body of a subject captured by the imaging system in order to extract image features in the third coordinate system; and
    joining the extracted image features with location data captured by the location tracking system by applying the third coordinate transformation,
    further comprising the steps of:
    a registration step, wherein an MRI scanner and the location tracking system are registered with each other,
    a second coordinate transformation step, wherein a processor calculates the second coordinate transformation between the second coordinate system and the first coordinate system, wherein the second coordinate system is a device coordinate system and the first coordinate system is a location coordinate system, a patient insertion step, wherein the body of the subject is inserted into the MRI scanner, a volume of interest step, wherein a low-resolution scan of the body of the subject is performed using the MRI scanner, and wherein an operator defines, using a control console, a volume of interest as a volume for subsequent high-resolution MRI scans, a first coordinate transformation step, wherein the first coordinate transformation is calculated between the second coordinate system and the third coordinate system, wherein the third coordinate system is a patient coordinate system, a third coordinate transformation step, wherein the third coordinate transformation is calculated between the first coordinate system and the third coordinate system as a product of the first coordinate transformation and the second coordinate transformation, a start step, wherein imaging of the body of the subject and location tracking are started, an MRI scan step wherein, the volume of interest is scanned by the MRI scanner with a high-resolution scan, an image generation step, comprising generating a medical image in the third coordinate system, a read step, wherein the medical image is read by the processor, in a processing step in which the medical image is further processed to produce a processed image, a tracking step, wherein location tracking of the catheter by the location tracking system is started, a location data step, wherein the location tracking produces location data in the first coordinate system, a transformation application step, wherein the third coordinate transformation is applied to the location data from the location data step, wherein the location data is transformed into Digital Imaging and Communications in Medicine (DICOM) protocol coordinates, and a combination step, wherein the processed image from the processing step and the location data in the Digital Imaging and Communications in Medicine (DICOM) protocol coordinates from the transformation application step are combined to create a joint image.

2. The method according to claim 1, wherein the location tracking system comprises a magnetic tracking system.

3. The method according to claim 2, wherein registering the first 3D image with the first coordinate system comprises inserting a jig comprising calibration targets into the medical imaging system, capturing the jig in the first 3D image, and measuring locations of the calibration targets.

4. The method according to claim 1, wherein the medical imaging system comprises a magnetic resonance imaging (MRI) system.

5. The method according to claim 1, wherein the medical imaging system comprises a computerized tomography (CT) system.

6. The method according to claim 1, wherein the third coordinate system is defined according to the Digital Imaging and Communications in Medicine (DICOM) protocol.

7. The method according to claim 6, wherein processing the second 3D image comprises reading and processing the second 3D image by a software application complying with the DICOM protocol.

8. The method according to claim 1, wherein processing the second 3D image comprises at least one of rotating and segmenting the image.

9. The method according to claim 1, wherein the location data captured by the location tracking system comprises a location of a distal end of a catheter within an anatomical structure in the body.

10. The method according to claim 1, wherein joining the extracted image features with location data comprises displaying the extracted image features and the location data concurrently on a display.

11. An apparatus for displaying registered images, the apparatus comprising:

a location tracking system, which is configured to map anatomical structures in a first coordinate system;

a medical imaging system, within which the location tracking system is installed in a fixed position, and which is configured to capture three-dimensional (3D) images of the anatomical structures in a second coordinate system, wherein the three-dimensional (3D) images are converted to and stored in a standardized format in a third coordinate system in accordance with a first coordinate transformation between the second coordinate system and the third coordinate system;

a processor configured to:

register a first 3D image captured by the imaging system with the first coordinate system so as to produce a second coordinate transformation between the first coordinate system and the second coordinate system;

combine the first coordinate transformation and the second coordinate transformation so as to derive a third coordinate transformation between the first coordinate system and the third coordinate system;

process a second 3D image of a body of a subject captured by the imaging system in order to extract image features in the third coordinate system; and join the extracted image features with location data captured by the location tracking system after applying the third coordinate transformation to the location data, wherein the apparatus is configured to be employed in performance of the following steps:

a registration step, wherein an MRI scanner and the location tracking system are registered with each other, a second coordinate transformation step, wherein a processor calculates the second coordinate transformation between the second coordinate system and the first coordinate system, wherein the second coordinate system is a device coordinate system and the first coordinate system is a location coordinate system, a patient insertion step, wherein the body of the subject is inserted into the MRI scanner, a volume of interest step, wherein a low-resolution scan of the body of the subject is performed using the MRI scanner, and wherein an operator defines, using a control console, a volume of interest as a volume for subsequent high-resolution MRI scans, a first coordinate transformation step, wherein the first coordinate transformation is calculated between the second coordinate system and the third coordinate system, wherein the third coordinate system is a patient coordinate system, a third coordinate transformation step, wherein the third coordinate transformation is calculated between the first coordinate system and the third coordinate system as a product of the first coordinate transformation and the second coordinate transformation, a start step, wherein imaging of the body of the subject and location tracking are started, an MRI scan step wherein, the volume of interest is scanned by the MRI scanner with a high-resolution scan, an image generation step, comprising generating a medical image in the third coordinate system, a read step, wherein the medical image is read by the processor, in a processing step in which the medical image is further processed to produce a processed image, a tracking step, wherein location tracking of the catheter by the location tracking system is started, a location data step, wherein the location tracking produces location data in the first coordinate system, a transformation application step, wherein the third coordinate transformation is applied to the location data from the location data step, wherein the location data is transformed into Digital Imaging and Communications in Medicine (DICOM) protocol coordinates, and a combination step, wherein the processed image from the processing step and the location data in the Digital Imaging and Communications in Medicine (DICOM) protocol coordinates from the transformation application step are combined to create a joint image.

12. The apparatus according to claim 11, wherein the location tracking system comprises a magnetic tracking system.

13. The apparatus according to claim 12, wherein the first 3D image is registered with the first coordinate system by inserting a jig comprising calibration targets into the medical imaging system, capturing the jig in the first 3D image, and measuring locations of the calibration targets.

14. The apparatus according to claim 13, wherein the third coordinate system is defined according to the Digital Imaging and Communications in Medicine (DICOM) protocol.

15. The apparatus according to claim 14, wherein the processor is configured to read and process the second 3D image using a software complying with the DICOM protocol.

16. The apparatus according to claim 11, wherein the medical imaging system comprises a magnetic resonance imaging (MRI) system.

17. The apparatus according to claim 11, wherein the medical imaging system comprises a computerized tomography (CT) system.

18. The apparatus according to claim 11, wherein processing the second 3D image comprises at least one of rotating and segmenting of the image.

19. The apparatus according to claim 11, wherein the location data captured by the location tracking system comprises the location of a distal end of a catheter within an anatomical structure in the body.

20. The apparatus according to claim 11, wherein the processor is configured to display the extracted image features concurrently with the location data on a display.

* * * * *